United States Patent
Wong, Sr.

(10) Patent No.: US 9,031,671 B2
(45) Date of Patent: May 12, 2015

(54) MEDICAL IMPLANTABLE LEAD AND MANUFACTURE THEREOF

(71) Applicant: Composite Materials Technology, Inc., Shrewsbury, MA (US)

(72) Inventor: James Wong, Sr., Shrewsbury, MA (US)

(73) Assignee: Composite Materials Technology, Inc., Shrewsbury, MA (US)

( * ) Notice: Subject to any disclaimer, the term of this patent is extended or adjusted under 35 U.S.C. 154(b) by 0 days.

(21) Appl. No.: 14/494,940

(22) Filed: Sep. 24, 2014

(65) Prior Publication Data

US 2015/0012078 A1    Jan. 8, 2015

Related U.S. Application Data

(63) Continuation-in-part of application No. 14/030,840, filed on Sep. 18, 2013, now abandoned.

(60) Provisional application No. 61/704,322, filed on Sep. 21, 2012.

(51) Int. Cl.
*A61N 1/05*    (2006.01)
*H01B 7/04*    (2006.01)

(52) U.S. Cl.
CPC ............. *A61N 1/05* (2013.01); *Y10T 29/49208* (2015.01); *A61N 1/056* (2013.01); *H01B 7/048* (2013.01)

(58) Field of Classification Search
CPC ...................................................... H01B 7/048
See application file for complete search history.

(56) References Cited

U.S. PATENT DOCUMENTS

| | | | |
|---|---|---|---|
| 3,557,795 A | 1/1971 | Hirsch | 128/335.5 |
| 3,677,795 A | 7/1972 | Bokros et al. | 117/46 |
| 4,149,277 A | 4/1979 | Bokros | 3/1 |
| 4,846,834 A | 7/1989 | Von Recum et al. | 623/11 |
| 4,945,342 A | 7/1990 | Steinemann | 174/113 |
| 4,983,184 A | 1/1991 | Steinemann | 623/66 |
| 5,030,233 A | 7/1991 | Ducheyne | 623/16 |
| 5,231,996 A * | 8/1993 | Bardy et al. | 607/126 |
| 5,324,328 A | 6/1994 | Li et al. | 607/129 |
| 5,869,196 A | 2/1999 | Wong et al. | 428/613 |
| 6,648,903 B1 | 11/2003 | Pierson | 602/232 |
| 6,728,579 B1 | 4/2004 | Lindgren et al. | 607/116 |
| 6,792,316 B2 | 9/2004 | Sass | 607/116 |
| 6,980,865 B1 | 12/2005 | Wang et al. | 607/121 |

(Continued)

FOREIGN PATENT DOCUMENTS

| | | | | |
|---|---|---|---|---|
| WO | WO 2008/039707 | 4/2008 | | H01G 9/00 |
| WO | WO 2008/063526 | 5/2008 | | B22F 1/00 |
| WO | WO 2009/082631 | 7/2009 | | H01G 9/00 |

OTHER PUBLICATIONS

PCT International Search Report and Written Opinion issued in corresponding application No. PCT/US13/60702, dated Dec. 5, 2013 (9 pgs).

(Continued)

*Primary Examiner* — Michael Kahelin
(74) *Attorney, Agent, or Firm* — Hayes Soloway P.C.

(57) ABSTRACT

A medical implantable lead comprising a core formed of a bare conductive wire formed from a biocompatible, corrosion-resistant conductive material, loosely wrapped in a fibrous material formed of shaped flattened ribbon filaments of a valve metal, and surrounded by a biocompatible insulation material.

9 Claims, 2 Drawing Sheets

(56) References Cited

U.S. PATENT DOCUMENTS

| | | | |
|---|---|---|---|
| 7,020,947 B2 | 4/2006 | Bradley | 29/515 |
| 7,146,709 B2 | 12/2006 | Wong | 29/599 |
| 7,158,837 B2 | 1/2007 | Osypka et al. | 607/122 |
| 7,235,096 B1 | 6/2007 | Van Tassel et al. | 623/1.15 |
| 7,480,978 B1 | 1/2009 | Wong | 29/599 |
| 7,490,396 B2 | 2/2009 | Bradley | 29/515 |
| 8,224,457 B2 | 7/2012 | Strandberg et al. | 607/116 |
| 2004/0121290 A1 | 6/2004 | Minevski et al. | 433/201.1 |
| 2006/0195188 A1 | 8/2006 | O'Driscoll et al. | 623/14.12 |
| 2007/0093834 A1 | 4/2007 | Stevens et al. | 606/69 |
| 2007/0214857 A1 | 9/2007 | Wong et al. | 72/275 |
| 2007/0244548 A1 | 10/2007 | Myers et al. | 623/1.42 |
| 2008/0234752 A1 | 9/2008 | Dahners | 606/291 |
| 2009/0018643 A1 | 1/2009 | Hashi et al. | 623/1.15 |
| 2009/0075863 A1 | 3/2009 | O'Driscoll et al. | 514/3 |
| 2009/0095130 A1 | 4/2009 | Smokovich et al. | 75/356 |
| 2009/0187258 A1 | 7/2009 | Ip et al. | 623/23.72 |
| 2009/0228021 A1 | 9/2009 | Leung | 606/139 |
| 2009/0234384 A1 | 9/2009 | Hadba | 606/215 |
| 2010/0075168 A1 | 3/2010 | Schaffer | 428/544 |
| 2010/0280584 A1 | 11/2010 | Johnson et al. | 607/116 |
| 2011/0082564 A1 | 4/2011 | Liu et al. | 623/23.72 |
| 2011/0137419 A1 | 6/2011 | Wong | 623/16.11 |
| 2012/0239162 A1 | 9/2012 | Liu | 623/23.74 |
| 2013/0282088 A1 | 10/2013 | Bondhus | 607/116 |

OTHER PUBLICATIONS

Meier et al., "Cardiologist Issues Alert on St. Jude Heart Device," The New York Times, Business Day section, Aug. 22, 2012, pp. B1-B2 (2 pgs).

Journal article by Yarlagadda et al. entitled "Recent Advances and Current Developments in Tissue Scaffolding" published un Bio-Medical Materials and Engineering 2005 15(3), pp. 159-177.

International Search Report and Written Opinion issued in PCT/US2010/059124, dated Feb. 15, 2011.

International Preliminary Report on Patentability issued in PCT/US2010/059124, dated Jun. 14, 2012.

Grifatini, K., "Nervy Repair Job," Technology Review, Jan./Feb. 2010, pp. 80-82 (3 pgs).

Markaki et al. "Magneto-mechanical stimulation of bone growth in a bonded array of ferromagnetic fibres," Biomaterials 25, 2004, pp. 4805-4815 (11 pgs).

Li et al., "Ti6Ta4Sn Alloy and Subsequent Scaffolding for Bone Tissue Engineering," Tissue Engineering: Part A, vol. 15, No. 10, 2009, pp. 3151-3159 (9 pgs).

Ryan et al., "Fabrication methods of porous metals for use in orthopaedic applications" Biomaterials 27, 2006, pp. 2651-2670 (20 pgs).

Wang., M., "Composite Scaffolds for Bone Tissue Engineering," American Journal of Biochemistry and Biotechnology 2 (2), 2006, pp. 80-83 (4 pgs).

Wang et al., "Biomimetic Modification of Porous TiNbZr Alloy Scaffold for Bone Tissue Engineering," Tissue Engineering: Part A, vol. 00, No. 00, 2009 pp. 1-8 (8 pgs).

Extended European Search Report issued in related application No. 10835252.7, dated May 12, 2014 (7 pgs).

Office Action issued in related U.S. Appl. No. 12/961,209, dated Jul. 5, 2012 (12 pgs).

Office Action issued in related U.S. Appl. No. 13/713,885, dated May 10, 2013 (12 pgs).

Office Action issued in related U.S. Appl. No. 13/713,885, dated Aug. 8, 2013 (7 pgs).

Office Action issued in related U.S. Appl. No. 13/713,885, dated Oct. 30, 2013 (11 pgs).

Office Action issued in related U.S. Appl. No. 14/030,840, dated Jul. 17, 2014 (13 pgs).

Office Action issued in related U.S. Appl. No. 14/030,840, dated Apr. 9, 2014 (13 pgs).

Office Action issued in related U.S. Appl. No. 14/030,840, dated Dec. 13, 2013 (9 pgs).

Office Action issued in related U.S. Appl. No. 14/174,628, dated Jun. 10, 2014 (19 pgs).

Office Action issued in U.S. Appl. No. 14/328,567, dated Feb. 25, 2015 (24 pgs).

* cited by examiner

MEDICAL IMPLANTABLE LEAD AND MANUFACTURE THEREOF

CROSS REFERENCE TO RELATED APPLICATION

This application is a continuation-in-part of my co-pending U.S. application Ser. No. 14/030,840 filed Sep. 18, 2013, which application in turn claims priority from U.S. Provisional Application Ser. No. 61/704,322, filed Sep. 21, 2012, the contents of which are incorporated herein by reference.

BACKGROUND

The present invention relates to medical electrode leads and methods of manufacture thereof. The invention has particular utility in connection with cardiac pacing and defibrillation leads, i.e. suitable for intercardial stimulation of the heart with the help of an implantable pacemaker or defibrillator, and will be described in connection with such utility, although other utilities are contemplated.

Surgically implanted cardiac devices play an important role in the treatment of heart disease. In the 50 years since the first pacemaker was implanted, technology has improved dramatically, and these devices have saved or improved the quality of countless lives. Pacemakers treat slow heart rhythms by increasing the heart rate or by coordinating the heart's contraction for some heart failure patients. Implantable cardioverter defibrillators stop dangerous rapid heart rhythms by delivering an electric shock. As the range of applications widens, the number of patients with cardiac devices continues to increase. Approximately 400,000 devices are implanted each year in the United States, and there are >3 million patients with implanted cardiac devices currently living in the United States.

Surgically implanted cardiac devices comprise two main parts, the pulse generator, a metal package that contains electric circuits and a battery, which usually is placed under the skin or on the chest beneath the collarbone, and the wires, or leads, which run between the pulse generator and the heart. In a pacemaker, these leads allow the device to control the heart rate by delivering small busts of electric energy. In a defibrillator, the leads allow the device to deliver a high-energy shock and convert dangerous rapid rhythms (ventricular tachycardia or fibrillation) back to a normal rhythm.

Although leads are designed to be implanted permanently in the body, occasionally leads fail due, for example, to a break in the insulation. In fact, in the last several years, two major manufacturers, Medtronic and St. Jude have recalled cardiac leads due to insulation failure or short circuit.

Cardiac leads typically are formed of concentrically stranded small via wires 2 formed from biocompatible, corrosion resistant, conductive materials such as MP 35 N, a cobalt based alloy having a nominal composition of 35% Ni, 35% Co, 20% Cr and 10% Mo around a conductive biocompatible, corrosion-resistant core 4 formed of, e.g. silver (FIG. 1). A typical lead is constructed with seven strands of MP35 N at 0.005 inches (127 microns) in diameter, cabled, and then formed into a helical spring shape hollow cable or coil as shown in FIG. 2. Other cobalt-chromium alloys also have been used. This cable assembly is then electrically insulated with a suitable dielectric material 6 such as polyethylene or silicone rubber. The insulation also must be biocompatible and corrosion resistant. Most important, the insulation must be flexible and abrasion resistant in order to survive the tens of millions of flexure cycles the leads would be exposed to over the lifetime of a patient.

Failure of prior art cardiac leads typically is as a result of failure of the insulation due to abrasion by the coil. That is to say, a major factor contributing to the insulation failure is due to the design of the hollow lead cable. As can be seen in FIG. 2, the outer strands in contact with the insulation are extensively corrugated and oriented transverse to the axis of the cable. So rather than sliding, the insulation is abraded, by the multiple exposed strands of the hard MP 35N metal wires and excessive wear can occur at tight bends and turns. Thus, while the conductive wires or fibers typically do not fracture, through continuous flexure and bending especially at tight bends and turns, the conductive wires or sheath material would sometimes wear and break through the insulation. As reported in the New York Times, Business Day Section, Wednesday, Aug. 22, 2012, Page B1; the lead failure was due to "inside out" abrasion where the wires had pushed through from the inside. Prior attempts to address the break-through problem, i.e., in terms of improving insulation composition and insulation thickness, have not proved to be entirely satisfactory. Making the insulation thicker will make the lead more robust; however, making the insulation thicker compromises flexibility which may present problems to the surgeon during implantation. Also, the leads must be sufficiently flexible once implanted so as to not exert stress on or injure body parts surrounding the implanted electrode.

SUMMARY OF THE INVENTION

The present invention overcomes the aforesaid and other problems of the prior art, by providing an intermediate fibrous layer, formed e.g., of shaped metal flattened ribbon filaments of a biocompatible valve metal loosely wrapped around and between the bare conductive cable and the insulating layer. The intermediate fibrous layer which preferably is in the form of a braided fibrous material of shaped metal flattened filaments provides a smooth and cushioning layer and a lubricity which reduces insulation wear, and thus reduces lead failure.

The intermediate fibrous layer of shaped metal flattened ribbon filaments of biocompatible valve metal material may be formed quite thin, typically 2 to 50 microns in thickness, preferable 10 to 25 microns, most preferably about 5 to 10 microns in thickness.

The preferred valve metal comprises tantalum, although other valve metals such as niobium, titanium and zirconium which are also biocompatible, advantageously may be used in accordance with the present invention.

The fibrous valve metal layer is formed from shaped metal flattened ribbon filaments following the teachings of my prior U.S. Pat. Nos. 5,869,196 and 7,480,978, the contents of which are incorporated hereby by reference.

The process starts with fabrication of valve metal coated wire or filaments, by combining shaped elements of tantalum with a ductile material such as copper to form a billet. The billet is then sealed in an extrusion can, extruded, drawn and worked through a series of reduction steps to form thin flattened ribbons of valve metal following the teachings of my aforesaid U.S. Pat. Nos. 5,869,196 and 7,480,978.

The flattened ribbons are then formed into a mat or braid which is then loosely wrapped over a conventionally formed bare cardiac lead. If the ribbons are placed directly in an insulation covered cardiac lead, abrasion can occur at the surface of this insulation and result in electrical failures of the lead. For this reason, the insulation layer is placed on top of the bare wrapped mat or braid.

BRIEF DESCRIPTION OF THE DRAWINGS

Further features and advantages of the present invention will be seen from the following detailed description taken in conjunction with the accompanying drawings, wherein.

DETAILED DESCRIPTION

Figure 3:
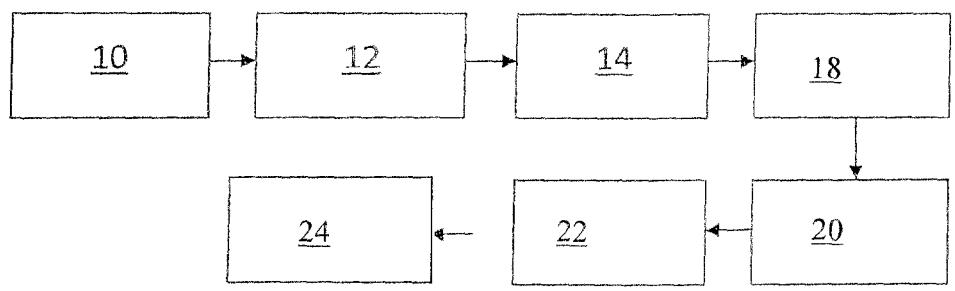
FIG. 3 diagramatically shows the overall process for forming an insulated wrapped lead in accordance with the present invention.
Figure 4:
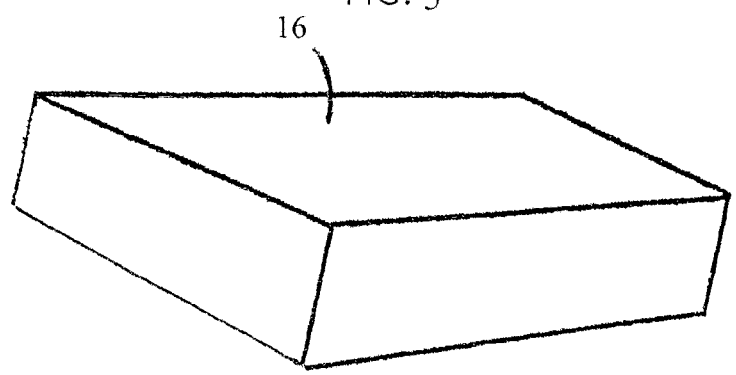
FIG. 4 is a schematic depiction of a flattened ribbon product used in forming a wrap in accordance with the present invention.

Referring to FIGS. 3 and 4. the process starts with the fabrication of valve metal filaments, such as tantalum, by combining shaped elements of tantalum with a ductile material, such as copper to form a billet at step 10. The billet is then sealed in an extrusion can, at step 12, and extruded and drawn in step 14 following the teachings of my prior U.S. Pat. Nos. 5,869,196 and 7,480,978. The resulting filaments are then restacked, extruded, drawn, etched and shaped into flattened ribbons 16 in step 18, following the teachings of my aforesaid U.S. Pat. Nos. 5,869,196 and 7,480,978

The filaments are formed into braids or a mat in step 20, following the teachings of my aforesaid U.S. Pat. Nos. 5,869, 196 and 7,480,978, which are then loosely wrapped around a bare conventional spiral helical cable lead in step 22. An insulation layer is then formed over the wrapped cable in step 24.

Figure 1:
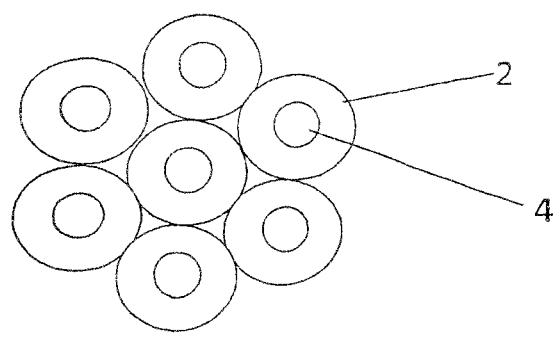
FIG. 1 diagram of MP35 N wire including a silver core.
Figure 2:
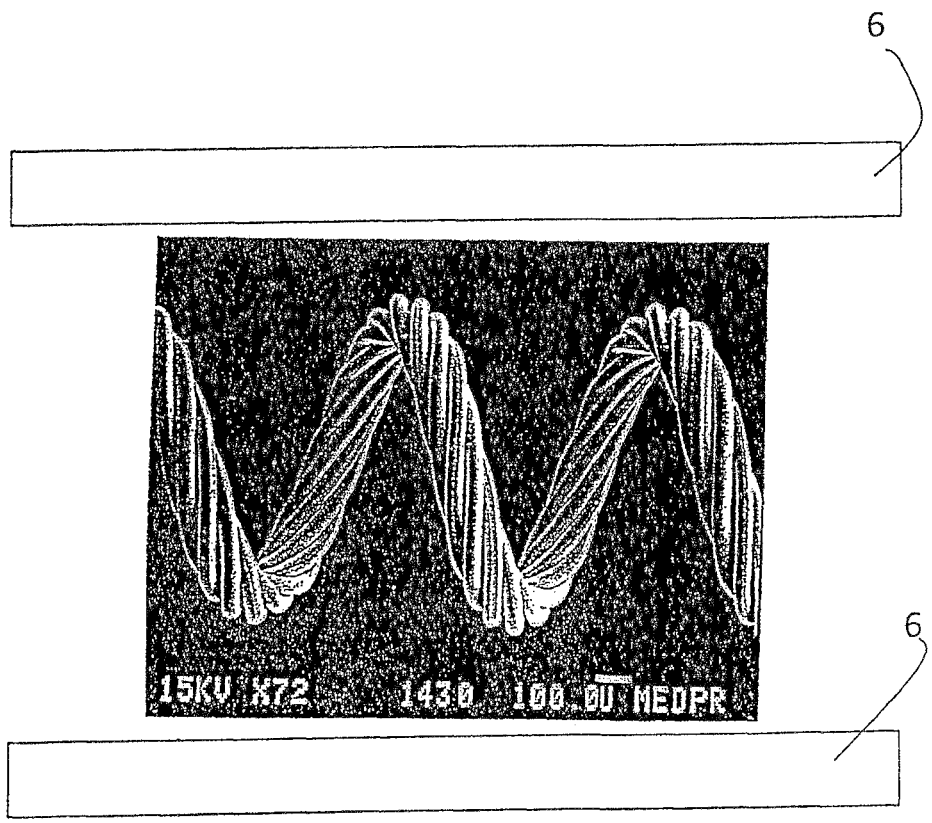
FIG. 2 shows the spiral helical cable lead.
Figure 5:
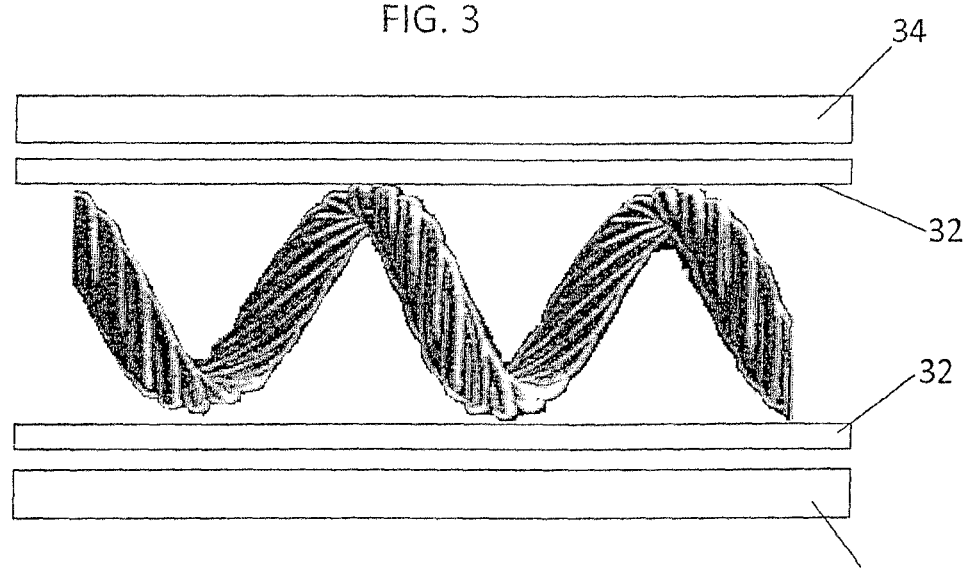
FIG. 5 shows an insulated, wrapped lead in accordance with the present invention.

Referring to FIG. 5, the resulting cable comprises a strand of silver core wire, spiral wound cable, (see FIG. 2) surrounded by a loosely wrapped mat or braid layer 32 of the flattened ribbons 16 of tantalum fibers, surrounded by insulation 34.

A feature and advantage of the present invention is that the wrap formed of shaped flattened ribbon filaments of tantalum or other valve metal, formed into a fiber braid or mat or other valve metal forms a smooth, relatively soft ductile sleeve that provides a cushion and a lubricity which reduces pressure and rubbing on the insulation from the underlying bare wire as the lead is flexed. In other words, the valve metal fiber wrap is put where it is most needed. As a result, the wire and the insulation are permitted to slide relative to one another. thus reducing wear and a potential for insulation breakthrough.

The present invention provides significant improvements over prior art medical implantable leads by providing a valve metal fiber wrap surrounding the metallic lead cable resulting in an extremely flexible lead, and which eliminates the abrasion and wear situation that exist with current medical implantable leads.

The invention claimed is:

1. A medical implantable lead comprising a core formed of a bare conductive wire formed from a biocompatible, corrosion-resistant conductive material, loosely wrapped in a fibrous material, formed of shaped flattened ribbon filaments formed of a valve metal selected from the group consisting of niobium, tantalum and zirconium, and surrounded by a biocompatible insulation material, said loosely wrapped fibrous material forming a smooth, ductile sleeve that provides a cushion and lubricity which reduces pressure and rubbing on the insulation from the underlying bare conductive wire as the lead is flexed.

2. The lead of claim 1, wherein the core comprises a metal core surrounded by a stranded metal cable.

3. The lead of claim 2, wherein the metal core comprises silver.

4. The lead of claim 2, wherein the stranded metal cable comprises a cobalt-chromium alloy material.

5. The lead of claim 1, wherein the fibrous material has a thickness of 2-50 microns.

6. The wire of claim 1, wherein the fibrous material has a thickness of 10-25 microns.

7. The wire of claim 1, wherein the fibrous material has a thickness of 5-10 microns.

8. A medical implantable lead comprising a cable formed of a biocompatible bare metal core, a wrap formed of a fibrous material formed of shaped flattened ribbon filaments formed of a valve metal selected from the group consisting of niobium, tantalum and zirconium, loosely surrounding the bare metal core, and an insulating layer surrounding the wrap, said loosely wrapped fibrous material forming a smooth, ductile sleeve that provides a cushion and lubricity which reduces pressure and rubbing on the insulation from the underlying bare metal core as the lead is flexed.

9. A method for forming a medical implantable lead comprising providing a bare lead cable formed of a biocompatible, corrosion-resistant conductive metal, loosely wrapping the bare lead cable with a biocompatible, fibrous material formed of shaped flattened ribbon filaments formed of a valve metal selected from the group consisting of niobium, tantalum and zirconium, and encasing the resulting wrapped structure with an electrical insulation layer, said loosely wrapped fibrous material forming a smooth, ductile sleeve that provides a cushion and lubricity which reduces pressure and rubbing on the insulation from the underlying bare lead cable as the lead is flexed.

\* \* \* \* \*